US00PP29626P3

(12) United States Plant Patent
Salman

(10) Patent No.: US PP29,626 P3
(45) Date of Patent: Aug. 28, 2018

(54) RED YUCCA PLANT NAMED 'CORAL GLOW'

(50) Latin Name: *Hesperaloe parviflora*
Varietal Denomination: Coral Glow

(71) Applicant: David Mark Salman, Santa Fe, NM (US)

(72) Inventor: David Mark Salman, Santa Fe, NM (US)

(73) Assignee: Waterwise Gardening, LLC, Santa Fe, NM (US)

( * ) Notice: Subject to any disclaimer, the term of this patent is extended or adjusted under 35 U.S.C. 154(b) by 0 days.

(21) Appl. No.: 15/330,736

(22) Filed: Oct. 31, 2016

(65) Prior Publication Data

US 2018/0124976 P1 May 3, 2018

(51) Int. Cl.
*A01H 5/02* (2018.01)
*A01H 5/12* (2018.01)

(52) U.S. Cl.
USPC ..... Plt./263.1
CPC ..... *A01H 5/0272* (2013.01); *A01H 5/12* (2013.01)

(58) Field of Classification Search
USPC ..... Plt./263.1
CPC ..... A01H 5/02; A01H 5/12; A01H 5/00
See application file for complete search history.

(56) References Cited

U.S. PATENT DOCUMENTS

PP21,728 P2 * 2/2011 Gass ..... A01H 5/02 Plt./263.1

OTHER PUBLICATIONS

High Country Gardens Gardening Tips and Know-How Award-Winning Everblooming *Hesperaloes* for Waterwise Beauty posted Jan. 19, 2016 retrieved on Oct. 23, 2017, retrieved from the Internet at https://www.highcountrygardens.com/gardening/everblooming-texas-red-yuccas/, 7 pp. (Year: 2016).*

Lady Bird Wildflower Center Plant Database *Hesperaloe parviflora* Apr. 2, 2016 retrieved on Oct. 24, 2017, retrieved from the Internet at https://www.wildflower.org/plants/result.php?id_plant=hepa8, 5pp. (Year: 2016).*

Missouri Botanical Garden *Hesperaloe parviflora* retrieved on Oct. 23, 2017, retrieved from the Internet at http://www.missouribotanicalgarden.org/PlantFinder/PlantFinderDetails.aspx?taxonid=281957&isprofile=0&cv=5,2 pp. (Year: 2017).*

High Country Gardens, "It's Here: Our 2016 Plant of the Year + 30 More Garden Tested Introductions", Catalog Distributed mid-Dec. 2015, 2 pages.

* cited by examiner

*Primary Examiner* — June Hwu

(57) ABSTRACT

A new and distinct plant variety of *Hesperaloe parviflora*, more commonly known as Texas red yucca, with long green to purple-red tipped stems having flowers exhibiting a unique coral-orange color on the outside of the petals and yellow in the interior of the petals.

2 Drawing Sheets

Latin name of the genus and species of the plant claimed: The ornamental plant variety of this invention is botanically identified as *Hesperaloe parviflora*.

Variety denomination: The variety denomination is 'Coral Glow'.

BACKGROUND OF THE INVENTION

The present invention relates to a new and distinct plant variety of *Hesperaloe parviflora*, more commonly known as Texas red yucca. The new variety has long purple-red stems with yellow and pink flowers.

Particularly in Southwestern United States, prolonged drought conditions and extended periods of extreme heat temperatures have expanded the commercial market for attractive, drought-tolerant, and vigorous ornamental plants. 'Coral Glow' provides a vibrant addition to landscapes.

'Coral Glow' was selected from several seedlings as the result of a cross between two garden plants. The female parent is *Hesperaloe parviflora* 'Yellow' (which is commercially available, unpatented) and the male parent is a *Hesperaloe parviflora* pink-red flowered specimen of unknown genetics (which is commercially available, unpatented).

'Coral Glow' was first asexually reproduced via tissue culture in Olympia, Wash. The tissue culture process involved taking meristem tissue from un-opened flower buds of the original plant and placing it onto agar using standard tissue culture protocols. 'Coral Glow' is moderately responsive to the tissue culture process, but is not as prolific as other cultivars, based on the lab's experience with the yellow flowered seed parent.

BRIEF SUMMARY OF THE INVENTION

Plant Breeder's Rights for this variety have not been applied for and 'Coral Glow' has not been offered for sale more than a year before the filing date of this application. 'Coral Glow' has not been promoted under any other breeder's reference or cultivar name.

Plants of 'Coral Glow' have not been observed wider all possible environmental and cultural conditions. The phenotype may vary somewhat with variations in environmental conditions, for example, with fluctuation in temperature, soil chemistry, and photoperiod without, however, any variance in genotype.

BRIEF DESCRIPTION OF THE PHOTOGRAPH(S)

The accompanying colored photographs illustrate the overall, typical appearance of the new and distinct red yucca plant showing the colors as true as it is reasonably possible to obtain in colored reproductions of conventional photography. Due to color variation reproduced in the photographs, color characteristics of this new variety should be determined with reference to the observations described herein, rather than a reliance on the photographs alone. Photographs were taken outdoors. The different photographs are intended to represent the distinctive characteristics of 'Coral Glow'.

Figure 1:
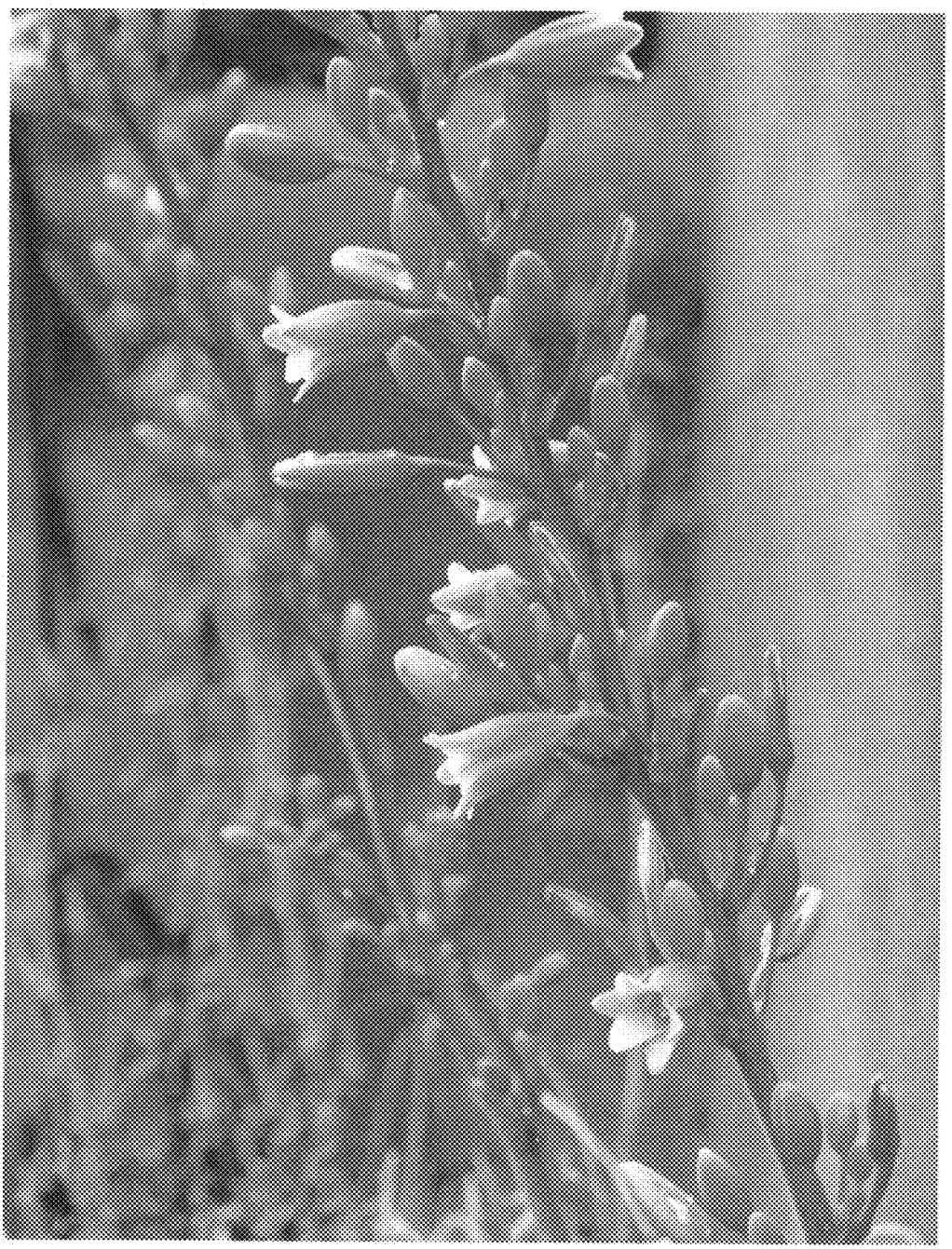

FIG. 1 (taken Jun. 13, 2015) is a close up view of the flowers and petals.

Figure 2:
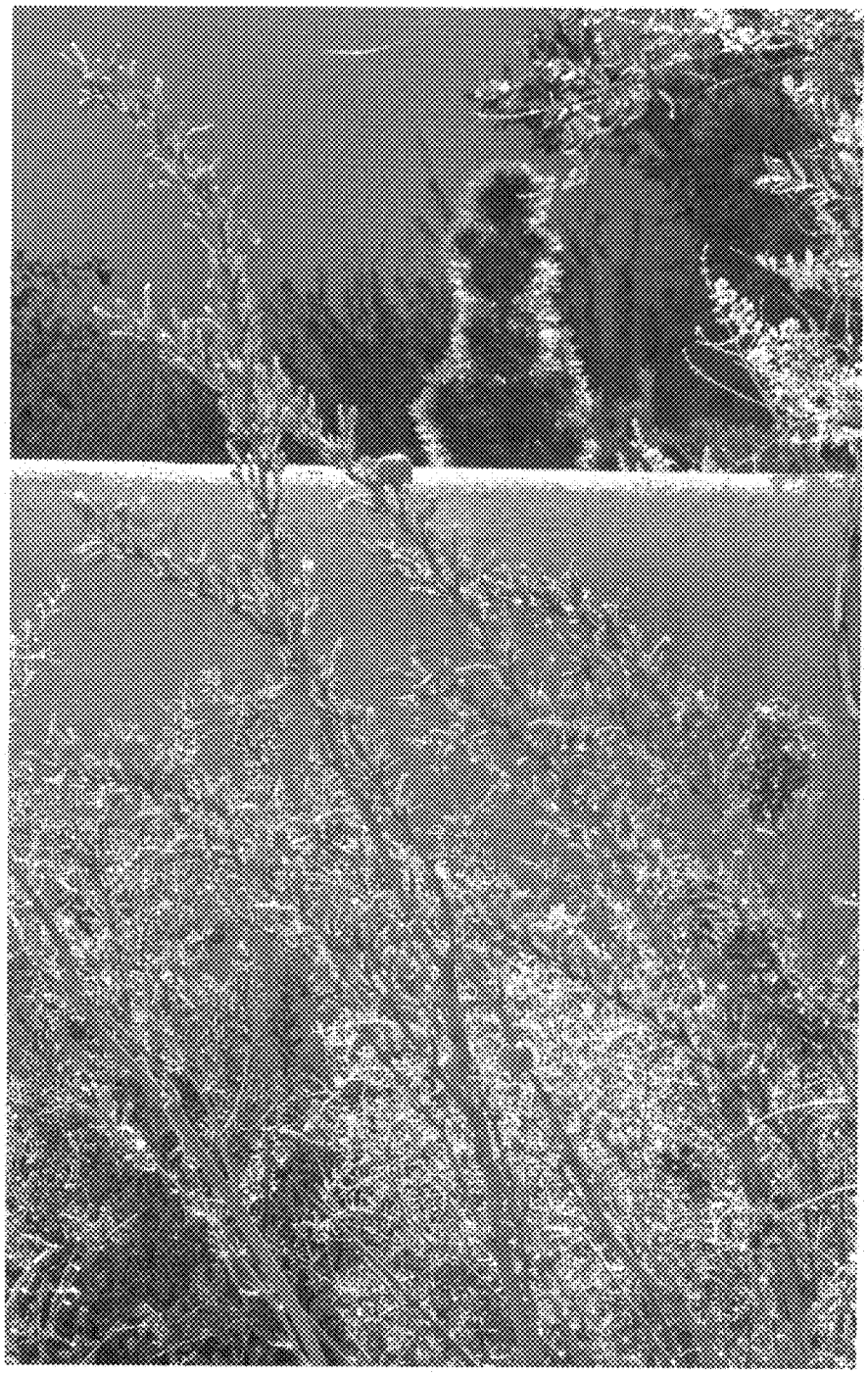

FIG. 2 (taken in Aug. 12, 2014) demonstrates the habit of the inflorescence.

DETAILED BOTANICAL DESCRIPTION

The following is a detailed description of the new variety 'Coral Glow' taken from plants about 10 years-in-age grown in an outdoor trail garden in Santa Fe, N. Mex. The color determinations are in accordance with the 2015 edition of The Royal Horticultural Society Colour Chart published by The Royal Horticultural Society (London, England), except where general color terms of ordinary dictionary significance.

VARIETY DESCRIPTION

Classification and utility:

*Botanical.*—*Hesperaloe parviflora.*

*Common.*—Texas Red Yucca or Hummingbird Yucca.

*Commercial classification.*—Ornamental shrub.

*Commercial use.*—Containers or landscape plant.

Parentage:

*Female.*—*Hesperaloe parviflora* 'Yellow' (commercially available, unpatented).

*Male.*—*Hesperaloe parviflora* pink-red flowered specimen of unknown genetics (commercially available, unpatented).

Plant:

*Plant type.*—Perennial evergreen succulent.

*Blooming period.*—From late spring until first frost (as observed in Santa Fe, N. Mex., United States located at 35.6870° N, 105.9378° W).

*Growth habit.*—Upright, clump-forming basal rosettes with numerous inflorescences held above the foliage.

*Growth rate.*—Moderate.

*Height and spread* (*average*).—1.1 in height and 1.0 m in spread (excluding peduncle, and 1.7 m in height, including peduncle).

*Branching habit.*—Stemless, leaves arranged in basal rosettes which clump close together with numerous inflorescences held above the foliage.

*Hardiness zone.*—USDA 5 to 9.

Leaf:

*Leaf shape.*—Gladiate, involute, and stiff.

*Leaf division.*—Simple.

*Leaf base.*—Clasping into a rosette, with new leaves emerging from the center of the leaf clump.

*Leaf arrangement.*—Basal rosette.

*Leaf apex.*—Narrowly acute.

*Leaf aspect.*—Upright and outwards to arching.

*Leaf venation.*—Parallel, inconspicuous, color; upper and lower surfaces matches leaf coloration.

*Leaf margins.*—Entire and fibrillose with curled fibrils. Color: RHS NN155C, evenly spaced along the length of the leaf.

*Leaf size* (*average*).—95.0 cm in length, 1.5 cm in width towards the base, and 3.0 mm in width towards the apex.

*Leaf surface.*—Inner and outer surfaces; glabrous, tough, and striate.

*Leaf number.*—An average of 12 leaves per rosette.

*Leaf color.*—Upper and lower surfaces (young and mature leaves): RHS 137B. Apex: Fading from RHS 144B to 144D towards the base with RHS 157B. Base: Very narrow stripe at the margin RHS 166B.

*Leaf attachment.*—Sessile to rosette base.

Flowers:

*Inflorescence type.*—Terminal upright with panicle bearing numerous single flowers. Flower fragrance: None. Flower type: Campanulate to tubular. Flower number (average): Approximately 650 flowers per inflorescence, with approximately 150 blooming at once. Inflorescence size (average): Height: 1.6 m (including peduncle) and 11.5 cm in diameter. Flower size (average): 2.2 cm in depth and 6.5 mm in diameter. Longevity of flowers (average): 3 days, self-cleaning (pedicels persistent). Flower aspect: Upwards when opening and outwards to nodding slightly downwards when fully open.

*Peduncle.*—Primary peduncle; 1 per rosette, strong and stiff, rounded in shape, held upright from basal rosette. Length (average): 72 cm. Width (average): 1.3 cm at the proximal end and 3 mm in width at the distal end. Color: RHS143C. Surface: Smooth, glabrous, and glaucescent. Internode length: Up to 14 cm. Stipule: 1 per node. Shape: Triangular. Apex: Acute. Base: Truncate and clasping. Surface: Smooth and glabrous. Color: RHS143C, fading to a blend between RHS197D and 199C. Persistent: Becoming papery.

*Secondary peduncle.*—Strong and flexible. Number (average): 5 per primary peduncle. Shape: Rounded. Angle (average): 20° to primary peduncle. Length (average): 17.0 mm. Width: 4.0 mm. Color: RHS143C. Surface: Smooth and glabrous.

*Pedicels.*—Primary pedicel: An average of 25 per secondary peduncle. Shape: Rounded. Angle (average): 30° to secondary peduncle. Length (average): 1.5 cm. Width (average): 4 mm in width. Color: RHS143C. Stipules: Present between secondary pedicels. Shape: Triangular. Surface: Thin and papery surface. Length (average): 3.0 mm. Width (average): 3.0 mm. Apex: Acute. Base: Truncate. Color: Blend between RHS 39B and 143D. Secondary pedicel: An average of 15 per primary pedicel (5 with flowers actively blooming). Shape: Rounded to oval. Angle (average): Flexible, angle of 10° to primary peduncle. Length (average): 1.0 cm. Width (average): 1.0 mm. Color: RHS39B fading to RHS199A to 199B. Surface: Smooth, glabrous, and shiny.

*Buds.*—Shape: Elliptic. Length (average): 1.5 cm. Width (average): 7.0 mm. Color: RHS39A to 39C. Surface: Glabrous, smooth, and shiny surface.

*Tepals*.—Number: 6 (3 inner and 3 outer). Shape: Elliptic. Apex: Acute. Base: Truncate. Margin: Entire. Surfaces (inner and outer): Surfaces glabrous, smooth, and satiny. Length (average): 1.5 cm. Width (average): 5.0 mm. Color: Outer tepals: Outer surface RHS39A to 39B, very lightly suffused with RHS11A and Inner surface RHS 11B to 11C, lightly suffused with RHS39A. Inner tepals: Outer surface: RHS39B to 39D with central stripe RHS39A and margins RHS11B, inner surface RHS11B to 11D suffused with RHS39B.

Reproductive organs:

*Gynoecium*.—Pistil Number: 1. Length (average): 5.0 mm. Stigma: Shape: Flattened disc shape. Color: RHSNN155D. Size: Minute. Style: Length (average): 5.0 mm. Width (average): 1.0 mm. Color: RHSNN155D. Ovary: Superior. Shape: Oval. Depth (average): 4.0 mm. Width (average): 3.0 mm. Color: RHSN144B to N144D with RHS150C at the apex.

*Androecium*.—Stamen number: 6. Anthers: Dorsifixed. Shape: Linear. Length (average): 3.7 mm. Width (average): 1 mm. Color: RHS8A. Filament: Length (average): 1.0 cm. Width (average): 1.0 mm. Color: RHSNN155C, suffused with RHS63B. Pollen: Not present.

*Fruit/seed*.—Not observed, plant is essentially sterile and only occasionally sets seed. Pods and seeds are typical for the species.

Propagation: Tissue culture for both propagation and maintenance.

*Time required for root development* (*average*).—28 to 30 days with rooted cutting produced after an average of 6 to 8 weeks.

*Description*.—Fibrous.

*Color*.—RHS 160B.

Best mode growing conditions:

*Water use/drought tolerance*.—Drought tolerant when planted in the ground.

*Fertilization*.—Use standard water soluble 15-15-15 or similar formulation every week to two weeks during growing season.

*Propagation*.—Using industry standard tissue culture protocols for *Hesperaloe parviflora*.

*Landscape cultivation*.—Top dressing of garden/landscape plants in fall with a blend of compost and good quality natural/organic fertilizer.

Disease and pest resistance: 'Coral Glow' does not seem to be prone to any diseases in cultivation, either in the tissue culture process or growing in the landscape. And the plant doesn't appear to have any increased resistance to common disease or insect pathogens. The flowers, like all *Hesperaloe*, are fed upon by common green aphids in the garden.

COMPARISON TO SIMILAR VARIETIES

*Hesperaloe* X 'Perfu' (U.S. Plant Pat. No. 21,728) Pink Parade, a hybrid between *Hesperaloe funifera* and *Hesperaloe parviflora*, has bright green foliage nearly one inch wide, and forms an upright clump of foliage 3 to 4 feet tall and wide. The 8-foot-tall branched flower spikes bear flowers with petals that have a bright pink exterior and light pink interior. The flower spikes are held strongly erect, forming a linear pink line when planted in rows. In contrast, 'Coral Glow' is not an interspecific hybrid, with both parents of the species *parviflora*. The foliage is narrower and olive-green in color, not bright green. 'Coral Glow' is smaller at mature size. The flower spikes are not as tall and not held erect, instead arching outward from the rosette of stems. The flowers are coral-orange in color, not pink.

*Hesperaloe parviflora* 'Perpa'Brakelights® (U.S. Plant Pat. No. 21,729) is a noticeably compact grower that forms an upright clump of narrow, blue-green leaves about 2 feet tall by 2 feet wide and blooms on short, 3 to 4-foot tall flower spikes bearing semi-double, vivid, red flowers with the petals having the same red color inside and out.

'Coral Glow', in contrast, is a larger plant at mature size both in the height and width of the rosette of foliage and the height of the flower spikes. The flowers are single in their petal arrangement and have a coral-orange exterior and yellow interior, not bright red.

'Coral Glow' differs from its seed parent, a yellow-flowered plant, primarily in its flower color being coral-orange color on the outside of the petals and yellow in the interior of the petals. 'Coral Glow' inherited the nearly sterile nature of its yellow flowered parent and is very similar in mature size. 'Coral Glow' is a smaller growing plant than the pink-red flowered pollen parent and its flower color, mentioned above is also visibly different from the pollen parent.

I claim:

1. A new and distinct variety of *Hesperaloe parviflora* plant, having the characteristics substantially as described and illustrated herein.

* * * * *